United States Patent [19]

Sanders

[11] Patent Number: 4,576,945

[45] Date of Patent: Mar. 18, 1986

[54] HEXAALKYLMELAMINE-AMINO-OXY COMPOUNDS

[76] Inventor: Mark E. Sanders, 1740 Shaleh Meadows Rd. Apt. 9D, Holladay, Utah 84117

[21] Appl. No.: 567,475

[22] Filed: Jan. 3, 1984

Related U.S. Application Data

[63] Continuation-in-part of Ser. No. 436,682, Oct. 26, 1982, abandoned.

[51] Int. Cl.⁴ .................... C07D 251/52; A61K 31/53
[52] U.S. Cl. .................................... 514/245; 544/196; 544/204
[58] Field of Search ............... 544/196, 204; 424/246; 514/245

[56] References Cited

FOREIGN PATENT DOCUMENTS 1025902  4/1966  United Kingdom ............... 544/196

OTHER PUBLICATIONS

Saunders et al., "Chemistry, Metabolism and Anti-Tumor Activity of Hexamethylmelamine-1-Oxide" 185th Melting ACS National Div. of Med. Chem., Seattle, Washington, Mar. 20–25, 1983, Abstract 84.

*Primary Examiner*—John M. Ford
*Attorney, Agent, or Firm*—Scully, Scott, Murphy & Presser

[57] ABSTRACT

Hexaalkylmelamine-amino-oxy compounds having antitumor properties and pharmaceutical compositions for and therapeutic methods of treatment of tumors and employing same.

19 Claims, No Drawings

HEXAALKYLMELAMINE-AMINO-OXY COMPOUNDS

CROSS REFERENCE TO RELATED APPLICATIONS

This application is a continuation-in-part of copending application Ser. No. 436,682, filed Oct. 26, 1982, now abandoned.

BACKGROUND OF THE INVENTION

The present invention relates to novel hexaalkylmelamine (HMM) derivatives having anti-tumor and metal chelating properties.

Hexamethylmelamine (HMM) is a well-known anticancer agent introduced for clinical trials in the early 1960's. The drug has been found to have significant activity against ovarian cancer and is also active against human pulmonary and renal tumors in mice. The concurrent use of HMM with cyclophosphamide, methotrexate and 5-fluorouracil has been found to be effective against advanced ovarian adenocarcinoma (Young et al., N. Engl. J. Med., Vol. 299, pp. 1261–1266 (1978)).

Hexamethylmelamine, when employed as an anticancer agent suffers from several disadvantages. It is generally administered orally but is poorly absorbed. Furthermore, it causes nausea and vomiting, myelosuppression and neurotoxicity.

A more soluble derivative, pentamethylmelamine, which is a major metabolite of HMM is in the early phases of clinical testing (Rutty et al., Biochem. Pharmacol, Vol. 26, pp. 2385–2391 (1977)).

It is an object of the present invention to provide a derivative of HMM and related compounds having anti-tumor properties as well as metal chelating properties which are more water soluble than and not subject to the same disadvantages of HMM.

SUMMARY OF THE INVENTION

The above and other objects are achieved by the present invention which provides a compound having the formula:

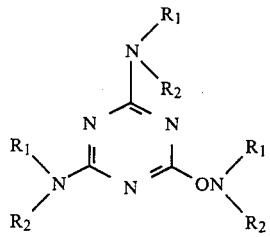

(1)

wherein $R_1$ and $R_2$ are independently lower alkyl. The alkyl groups may be straight chained or branched, and preferably contain from 1 to 8 carbon atoms.

The present invention also provides a pharmaceutical composition in unit dosage form especially adapted for the treatment of animals afflicted with tumor cells sensitive to a compound of the above formula (1) comprising an antitumor effective amount of a compound of formula (1) and a pharmaceutically acceptable carrier therefor.

The present invention also provides a method for the treatment of animals afflicted with tumor cells sensitive to a compound of formula (1) comprising administering to such an animal an antitumor effective amount of a compound of formula (1), preferably in the form of the above-described pharmaceutical composition.

The present invention also provides a method for preparing a compound of formula (1) comprising oxidizing the corresponding hexaalkylmelamine and recovering the amino-oxy compounds.

DETAILED DESCRIPTION OF THE INVENTION

The preferred compound according to the invention in the compound of the formula (1) namely, 2,4-bis(-dimethylamino)-6-[(dimethylamino)oxy]-1,3,5-triazine (O-HMM) having the formula:

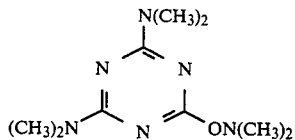

The compounds of the invention are prepared by oxidizing the corresponding hexaalkylmelamine with one of a variety of oxidizing agents. The most effective oxidizing agents are peroxy compounds, preferably organic acylhydroperoxides such as meta-chloroperoxybenzoic acid (MCPBA) and p-nitroperoxybenzoic acid (PNPBA). Other oxidizing reagent systems such as hydrogen peroxide/acetic acid, and hydrogen peroxide/trifluoroacetic acid may also be utilized; however, yields of the desired product are lower than with the preferred acylhydroperoxides due to the competing acid catalyzed side reaction rearrangement of the hexaalkymelamine amino-oxy compound to 2-hydroxy-4,6-bis(dialkylamino)-1,3,5-triazine (HDT).

Generally, the starting tertiary amine is reacted with a slight excess over the stoichiometric amount of oxidizing agent required to effect conversion to the amino-oxy compound. Whereas increasing amounts of oxidizing agent, particularly peracid increases the overall yield of the amino-oxy compounds, isolation and recovery difficulties are encountered. Accordingly, it is preferred to employ an amount of oxidizing agent in the range of from about 1 to about 3 mole equivalents, preferably from about 1.3 to 1.7 mole equivalents.

The reaction proceeds smoothly in the presence of a solvent such as chloroform, methylene chloride, 1,1,2-trichloroethane, 1,1,2,2-tetrachloroethane, benzene or ethyl acetate.

The temperature of the reaction mixture is not overly critical. Generally, temperatures in the range of from about 40° C. to about 70° C. for a period of time in the range of from about 14 hr. to about 26 hr. is sufficient to drive the reaction to completion. It will be understood by those skilled in the art that employing higher temperatures in the above-indicated range will require shorter reaction times whereas the lower temperatures require longer reaction times to complete the reaction.

The pharmaceutical compositions of the invention containing an amount of one of the above-described compounds effective against animal tumor cells sensitive thereto are preferably compounded in unit dosage form with a pharmaceutically acceptable carrier especially adapted for oral, intravenous or intraperitoneal administration.

Carriers suitable for oral administration include in addition to the pure drug any of the conventional carriers, e.g., lactose, mannitol, soluble starch, etc. Carriers suitable for intravenous and intraperitoneal administration include isotonic saline (0.9% NaCl in water), 5% Dextrose in water, etc.

The anti-tumor compound of the invention may be compounded with the above-noted carriers according to any of the well-known, conventional methods for preparing orally, intravenously or intraperitoneally administrable pharmaceutical compositions.

As is standard practice for the administration of all currently used standard and investigational drugs, O-HMM should not be mixed with with other drugs. In addition, O-HMM should not be exposed to elevated temperatures (>50° C.), strong mineral acids or salts of transition metals.

Suitable methods for the preparation of pharmaceutical compositions containing the anti-tumor compounds of the invention include those described in Pharmaceutical Dosage Forms, Vol. 1, Edited by Herbert A. Lieberman and Leon Lachman, Marcell Deker, Inc., New York, N.Y., 1980, and Theory and Practice of Industrial Pharmacy, Edited by Leon Lachman, Herbert A. Lieberman and Joseph L. Kanig, Lea and Sebiger, Inc., Philadelphia, Pa., 1976.

The unit dosage form of the pharmaceutical composition of the invention should contain from about 10 to about 1000 mg, preferably from 50 mg to 100 mg, of the amino-oxy compounds.

The animal afflicted with tumor cells sensitive to the compounds of the invention are preferably treated by administering the anti-tumor compound, preferably in the form of the above-described pharmaceutical composition, to the animal orally, intravenously or intraperitoneally.

Although the dosage required to affect the proliferation of tumor cells will depend in each case upon the particular type of tumor and its location within the body, generally, an amount of anti-tumor compound in the range of from about 10 to about 1000 mg/kg, preferably from 200 to 400 mg/kg, of body weight of the animal undergoing treatment is sufficient to affect the growth of the tumor. When utilizing the preferred compound, O-HMM to treat animals afflicted with human lung carcinoma, human bronchus carcinoma, human kidney carcinoma and human ovarian adenocarcinoma, it is generally preferred to administer a dosage between 200 and 400 mg/kg of body weight.

The compounds of the invention also find utility as a metal ion chelating agent, particularly for metal ions of the transition metal series (e.g., $Fe(II)$, $Fe(III)$, $Cu(I)$, $Cu(II)$, $Pt(IV)$, $Au(III)$, $Pb(II)$). The compounds may effectively be employed to remove such metal ions from any solution in which they are contained such as waste effluents, etc. The invention is illustrated by the following nonlimiting examples:

EXAMPLE 1

HMM (1 equivalent) is allowed to react with (1.5 equivalents) m-chloroperoxybenzoic acid (MCPBA) in chloroform at 55° C. for 20–24 hours. After the reaction period, the mixture is cooled and subjected to isolation procedures. O-HMM may be extracted from a basified aqueous system. The crude mixture is extracted with 5% $Na_2CO_3$/10% NaCl (for the purpose of removing unreacted MCPBA and m-chlorobenzoic acid; using 4 extractions of approximately one-third volume of the organic phase for each extraction). The organic phase is then dried with $Na_2SO_4$, filtered to remove drying agent and concentrated on a rotary evaporator (20 mm Hg). The viscous residue is then chromatographed on a column of silica gel (70–200 mesh, neutral grade, approximaately 75:1 silica:crude product weight) with ethyl acetate as solvent until unreacted HMM is eluted and most of the O-HMM has been eluted. After most of the O-HMM has eluted from the column, elution solvent is adjusted to 5% MeOH/EtOAc (v/v) to complete O-HMM elution and then to elute the more polar triazine-2-one rearrangement product. The O-HMM fractions are stripped of solvent to yield a white crystalline solid which may be recrystallized (from pentane) to yield pure O-HMM in 40–50% overall yield from HMM. M.P. (uncorrected) 79°–80° C. The HDT side reaction product was also isolated. M.P. (uncorrected) 296°–298° C.

NMR, IR and Mass spectral data for the principal amino-oxy product and its acid catalyzed rearrangement product, were consistent with structures for 2,4-bis(dimethylamino)-6-[(dimethylamino)oxy]-1,3,5-triazine and 2-hydroxy-4,6-bis(dimethylamino)-1,3,5-triazine, respectively. The structure of O-HMM has also been confirmed by X-ray crystallographic analysis.

The above procedure was repeated utilizing different reaction parameters, oxidizing agents and solvents. The reaction conditions and results are set forth in Table 1.

TABLE 1

| Peroxide | Solvent | Temp. | Time | HMM | O—HMM | HDT |
|---|---|---|---|---|---|---|
| MCPBA | $HCCl_3$ | 25° C. | 24 hr. | 86%[a] | 4% | 5% |
| MCPBA | $HCCl_3$ | 50° C. | 8 hr. | 64% | 14% | 19% |
| MCPBA | $HCCl_3$ | 50° C. | 24 hr. | 17% | 38% | 41% |
| p-$NO_2$PBA | $HCCl_3$ | 50° C. | 24 hr. | 21% | 27% | 49% |
| $H_2O_2$ | $CH_3CO_2H$ | 25° C. | 13 hr. | 45(73)[b] | 5(8)% | 12(19)% |

[a]Isolated yields
[b]Yields determined by NMR
MCPBA m-chloroperoxybenzoic acid
p-$NO_2$PBA p-nitroperoxybenzoic acid The conditions required for rearrangement of O-HMM to the HDT product are set forth in Table 2.

TABLE 2

| Solvent | Temp. | Time | HMM—NO | HDT |
|---|---|---|---|---|
| $HCCl_3$ | 25° C. | 26 hr. | 97%[a] | 3% |
|  | 50 | 26 | 63 | 37 |
|  | 135[b] | 20 | 0 | 100(97)[c] |
| $HCCl_3$/$H^+$[d] | 25 | 26 | 34 | 66 |
|  | 50 | 26 | 3 | 97 |
|  | 135[b] | 20 | 0 | 100(98) |
| $HCCl_3$/$H^+$[e] | 50 | 26 | 0 | 100 |
| Pentane | 135[b] | 20 | 0 | 100(99) |
| $H_2O$/$H^+$[f] | 25 | 4 | 21 | 79 |
|  | 50 | 4 | 0 | 100 |
| $H_2O$/$H^+$[g] | 25 | 4 | 0 | 100(98) |
| $H_2O$ | 25 | 24 | 100 | 0 |

| TABLE 2-continued | | | | |
|---|---|---|---|---|
| Solvent | Temp. | Time | HMM—NO | HDT |
| | 50 | 24 | 91 | 9 |

[a]Yields determined by NMR
[b]Sealed tube reaction. Solutions degassed with argon and then sealed under vacuum
[c]Isolated yield
[d]0.1 equiv. m-chlorobenzoic acid
[e]0.1 equiv. p-nitrobenzoic acid
[f]0.05 M HOAc/NaOAc pH 5
[g]0.01 M HCl O-HMM is soluble in both lipid (pentane, 29 mg/ml) and aqueous (water 19 mg/ml) media.

EXAMPLE 2

The identity of O-HMM was further verified by the following alternate method of synthesis:

In a 15 ml round bottom flask equipped with a water cooled West condenser, sealed with a rubber septum and mineral oil bubbler, was added 5 ml anhydrous triethylamine (distilled from BaO prior to use) followed by 242 mg (10 equivalents based on triazine, 2.48 mmoles) N,N-dimethylhydroxylamine hydrochloride (Aldrich) and 380 mg (10 equivalents, 2.48 mmoles) barium oxide (Alpha). To this mixture was then added 50 mg 2-chloro-4,6-bis(dimethylamino)-1,3,5-triazine (0.248 mmoles) in one portion. The reaction flask was then sealed with the rubber septum and flushed with argon. After stirring 24 hrs. at 60° C., the reaction mixture was cooled to room temperature and filtered through a small column of celite-545 using diethyl ether to wash flask and column. After removing solvents and volatiles on a roto-evaporator (25 mm) a white crystalline material was obtained which was further dried in vacuo (0.01 mm). Thin layer chromatography of the crude product mixture indicated, by comparison to authentic samples, the presence of hexamethylmelamine (HMM) O-HMM, 2-hydroxy-4,6-bis(dimethylamino)-1,3,5-triazine (HDT) and unidentified material at origin (0.25 mm silica-F254, 100% ethyl acetate and also using 80% ethyl acetate/10% pentane). $^1$H-NMR (DCCl$_3$) showed HMM (29%), O-HMM (31%) and HDT (39%). HPLC of this material (Whatman ODS-3, 25 cm, 10 u, 65% methanol/35% water) confirmed product ratios. Retention times were also compared with authentic samples of HMM, HDT and O-HMM (prepared by acylhydroperoxide oxidation of HMM). Low pressure preparative chromatography (silica, 100% ethyl acetate) was used to separate products for further identification. Chromatographic fractions 11 through 16 were combined and this product was shown by comparison (HPLC, TLC, $^1$H-NMR, MS) to be identical with O-HMM prepared by acylhydroperoxide oxidation of HMM.

Treatment of a portion of the material, obtained by preparative chromatography and identified as O-HHM, was subjected to acid hydrolysis and hydrogenolysis. Hydrolysis of this material with 1N HCl (50° C., 3 hr.) gave after isolation HDT as the only triazine product. Similarly, hydrogenolysis of this material (10% Pd-C, E+OAc, H$_2$, atmospheric pressure, room temperature 1.5 hr.) gave HDT as the only triazine product. No attempt was made to isolate the amine fragment lost during these reactions.

EXAMPLE 3

In vivo metabolism of O-HMM

Male Harlen-Sprague-Dawley rats, 200–300 g were given 20 mg/kg of O-HMM by intraperitoneal injection (control rats received saline vehicle only) and their urine collected for two consecutive 24 hr. periods. No acute toxic effects were observed after administration of O-HMM. Analyses of 24 hr. and 48 hr. urine samples show no significant recovery of the parent O-HMM or appearance of hexamethylmelamine HMM or its major dimethylation product pentamethylmelamine PMM. O-HMM was shown to be stable when incubated at 37° C. for 3 hours with water, human urine or rat urine as measured by substrate loss and appearance of other products, such as HMM, PMM and HDT.

EXAMPLE 4

Anti-cancer activity of O-HMM

Cytotoxic activity of O-HMM against in vitro human tumor cells was measured as inhibition of colony formation and the results expressed as a ratio of the number of colonies in test dishes to number of control dishes, times 100 (Table 4).

Complete inhibition of colony formation in A-549 lung carcinoma, A-101D melanoma, A-498 renal carcinoma and A-204 rhabdomysarcoma continuous human tumor cell assays was observed following long-term exposure (9 days) at a concentration of 200 μg/ml (Table 3). O-HMM shows consistently greater activity than HMM in these test systems.

TABLE 3

Inhibition of colony formation by human tumor cell lines exposed (9 days) to O—HMM and HMM[a]

| | A-204 | A-498 | A-101D | A-549 |
|---|---|---|---|---|
| O—HMM | | | | |
| 200 ug/ml | 0%[a] | 0% | 0% | 0% |
| 120 | 1 ± 2 | 5 ± 6 | 0 | 0 |
| 100 | 4 ± 4 | 14 ± 9 | 0 | 0 |
| 80 | 20 ± 17 | 24 ± 18 | 1 ± 1 | 0 |
| 60 | 48 ± 21 | 44 ± 23 | 17 ± 16 | 9 ± 14 |
| 40 | 76 ± 17 | 67 ± 14 | 50 ± 15 | 69 ± 11 |
| 20 | 87 ± 13 | 83 ± 7 | 82 ± 9 | 94 ± 4 |
| 10 | 99 ± 26 | 93 ± 3 | 95 ± 10 | 91 ± 6 |
| HMM.HCl | | | | |
| 225 ug/ml[b] | 40 ± 28 | 41 ± 8 | 29 ± 6 | |
| 200 | 38 ± 21 | 42 ± 19 | 33 ± 8 | 61 ± 19 |
| 175 | 38 ± 26 | 43 ± 25 | 38 ± 9 | 59 ± 23 |
| 150 | 35 ± 29 | 42 ± 18 | 37 ± 8 | 74 ± 17 |
| 100 | 55 ± 27 | 50 ± 12 | 53 ± 11 | 86 ± 9 |
| 75 | 62 ± 24 | 61 ± 12 | 73 ± 5 | 87 ± 11 |
| 50 | 78 ± 15 | 75 ± 8 | 92 ± 13 | 95 ± 8 |
| 25 | 85 ± 8 | 90 ± 12 | 98 ± 11 | 91 ± 12 |
| 20 | 104 ± 12 | 97 ± 6 | 101 ± 4 | 93 ± 4 |
| 10 | | | | 95 ± 5 |

[a]Percent survival as measured by the number of colonies in test dishes to colonies in control dishes times 100.
[b]At concentrations of HMM—HCl > 100 μg/ml solubility in buffered media may be a limiting factor.

Melamine anti-tumor agents, in particular HMM, have been studied in the clinic and laboratory for more than two decades. HMM is interesting in that it has no demonstrated activity in most N.C.I. animal anti-tumor screening systems, but nevertheless has demonstrated activity against human disease. The poor correlation between activity of anti-tumor agents in vivo animal model systems and activity against human disease has resulted in recent studies to evaluate alternate screening systems. The in vitro human tumor colony formation assay is currently being proposed as a potential alternate screening system for new compounds.

EXAMPLE 4

Toxicity study

LD$_{50}$ studies were conducted on male BDF$_1$ mice (17–21 g) at dosages of O-HMM of 1000, 500, 250, 100, 50 and 25 mg/kg of body weight. IP (4 mice in each dosage group) injection of O-HMM (aqueous solutions) exhibit a dose dependent toxic phenomenon showing a decreasing degree of a flaccid paralysis with decreasing dose. These effects diminished over a period of about 3–5 hours until the animal appeared normal and resumed activity. A dose-dependent time of recovery was also observed. The manifestation of toxic effect was very rapid with immediate changes in the mouse's behavior being observed in <1 minute after injection IP, thereby indicating a very rapid absorption of the O-HMM.

At 1000 mg/kg death occurred in 3 of the 4 mice in ≦3 minutes with the fourth mouse recovering completely.

All of the remaining mice in the other groups exhibited the above-noted, dose-dependent behavior but recovered completely in a few hours.

Long term 60- and 120-day observation of the mice treated with the above dosages showed no long-term effects over this time period as determined by weight loss, hair loss, and death rate as compared to control animals.

I claim:

1. A compound having the formula:

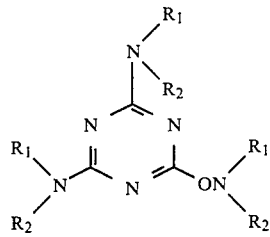

wherein R$_1$ and R$_2$ are independently lower alkyl.

2. A compound having the formula:

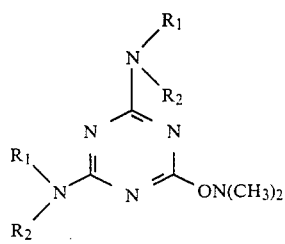

wherein R$_1$ and R$_2$ are independently lower alkyl.

3. The compound having the formula:

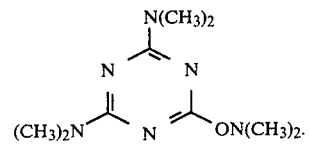

4. A pharmaceutical composition in unit dosage form containing from about 10 to about 1000 mg of a compound of claim 1 or claim 2 and a pharmaceutically acceptable carrier therefor.

5. A pharmaceutical composition in unit dosage form containing from about 10 to about 1000 mg of a compound of claim 3 and a pharmaceutically acceptable carrier therefor.

6. The pharmaceutical composition of claim 5 wherein said carrier is intravenously administrable.

7. The pharmaceutical composition of claim 5 wherein said intravenously administrable carrier is isotonic saline or 5% dextrose in water.

8. The pharmaceutical composition of claim 4 wherein said carrier is intravenously administrable.

9. The pharmaceutical composition of claim 4 wherein said intravenously administrable carrier is isotonic saline or 5% dextrose in water.

10. A method for limiting growth of tumor cells in an animal sensitive to a compound of claim 1 or claim 2 comprising administering to said animal an anti-tumor effective amount of a compound of claim 1 or claim 2.

11. A method for limiting growth of tumor cells in an animal sensitive to a compound of claim 3 comprising administering to said animal an anti-tumor effective amount of a compound of claim 3.

12. The method of claim 11 wherein from about 10 to about 1000 mg/kg body weight of said antitumor compound is administered to said animal.

13. The method of claim 11 wherein said anti-tumor compound is administered intravenously.

14. The method of claim 10 wherein from about 10 to about 1000 mg/kg body weight of said anti-tumor compound is administered to said animal.

15. The method of claim 10 wherein said anti-tumor compound is administered intravenously.

16. A method of preparing a compound of claim 1 or claim 2 comprising oxidizing, under acidic conditions and in the presence of an inert organic solvent, a compound of the formula

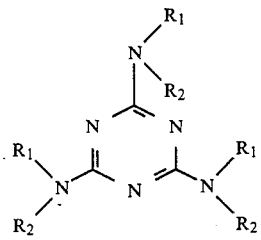

wherein R$_1$ and R$_2$ are independently lower alkyl.

17. The method of claim 16 wherein said oxidation is effected employing a peroxy compound as an oxidizing agent.

18. The method of claim 17 wherein said peroxy compound is an organic acylhydroperoxide.

19. The method of claim 18 wherein said organic acylhydroperoxide is meta-chloroperoxybenzoic acid or para-nitroperoxybenzoic acid.

* * * * *